US011180777B2

(12) United States Patent
Li et al.

(10) Patent No.: US 11,180,777 B2
(45) Date of Patent: Nov. 23, 2021

(54) CELL FRACTION AND METHOD OF GENERATING A CELL FRACTION CONTAINING A PROTEIN OF INTEREST

(71) Applicant: Corning Incorporated, Corning, NY (US)

(72) Inventors: Na Li, Winchester, MA (US); Jie Wang, Weston, MA (US)

(73) Assignee: Corning Incorporated, Corning, NY (US)

( * ) Notice: Subject to any disclaimer, the term of this patent is extended or adjusted under 35 U.S.C. 154(b) by 46 days.

(21) Appl. No.: 16/510,115

(22) Filed: Jul. 12, 2019

(65) Prior Publication Data

US 2020/0002726 A1 Jan. 2, 2020

Related U.S. Application Data

(62) Division of application No. 15/778,763, filed as application No. PCT/US2016/063292 on Nov. 22, 2016, now abandoned.

(60) Provisional application No. 62/259,788, filed on Nov. 25, 2015.

(51) Int. Cl.

| | |
|---|---|
| ***C12N 15/85*** | (2006.01) |
| ***C12N 15/88*** | (2006.01) |
| ***G01N 33/68*** | (2006.01) |
| *A61K 47/54* | (2017.01) |
| *C12N 13/00* | (2006.01) |

(52) U.S. Cl.

CPC ............ *C12N 15/88* (2013.01); *C12N 15/85* (2013.01); *G01N 33/6845* (2013.01); *A61K 47/543* (2017.08); *C12N 13/00* (2013.01); *C12N 2320/32* (2013.01); *G01N 2500/04* (2013.01)

(58) Field of Classification Search

CPC .... C12N 15/85; C12N 15/88; C12N 2320/32; C12N 13/00; G01N 33/6845; G01N 2500/04; A61K 47/543

See application file for complete search history.

(56) References Cited

U.S. PATENT DOCUMENTS

| | | | |
|---|---|---|---|
| 4,560,655 | A | 12/1985 | Baker |
| 4,657,886 | A | 4/1987 | Kolts |
| 4,767,704 | A | 8/1988 | Cleveland et al. |
| 4,927,762 | A | 5/1990 | Darfler |
| 5,122,469 | A | 6/1992 | Mather et al. |
| 5,672,502 | A | 9/1997 | Birch et al. |
| 6,048,728 | A | 4/2000 | Inlow et al. |
| 8,747,869 | B2 | 6/2014 | Irvine et al. |
| 2002/0082194 | A1 | 6/2002 | Guegler et al. |
| 2006/0024685 | A1 | 2/2006 | Ho et al. |
| 2012/0093885 | A1 | 4/2012 | Sahoo et al. |
| 2014/0080131 | A1 | 3/2014 | Yong et al. |
| 2015/0141634 | A1 | 5/2015 | Mitsuhashi |
| 2016/0102131 | A1 | 4/2016 | Li et al. |

FOREIGN PATENT DOCUMENTS

| | | | |
|---|---|---|---|
| JP | 2007-295929 | A | 11/2007 |
| JP | 2015-527088 | A | 9/2015 |
| WO | 2014043170 | A1 | 3/2014 |

OTHER PUBLICATIONS

Balliet RM, et al. (Apr. 1, 2009) Cancer Res. 69(7):2981-2989. (doi:10.1158/0008-5472.CAN-08-4143).*

Sun D, et al. (Nov. 2007) Drug Metabolism and Disposition. 35(11):2006-2014. (DOI: https://doi.org/10.1124/dmd.107.017145).*

Gorman CM, et al. (Nov. 11, 1983) Nucleic Acids Research. 11(21):7631-7648. (doi: 10.1093/nar/11.21.7631).*

Grunberg J, et al. (May 2003) Biotechniques. 34(5):968-972. (doi: 10.2144/03345st02).*

Goldstein S, et al. (May 25, 1989) Nucleic Acid Research. 17(10):3959-3971. (doi: 10.1093/nar/17.10.3959).*

Deng et al.; "Tandutinib (MLN518) Reverses Multidrug Resistance By Inhibiting the Efflux Activity of the Multidrug Resistance Protein 7 (ABCC10)"; Oncology Reports, 29; pp. 2479-2485; 2013.

Fujiwara et al.; "Interactions Between Human UGT1A1, UGT1A4, and UGT1A6 Affect Their Enzymatic Activities"; Drug Metabolism and Disposition 35, 1781-7, 2007.

International Search Report and Written Opinion of the International Searching Authority; PCT/US2016/063292; dated Mar. 29, 2017; 19 Pages; European Patent Office.

Invitation To Pay Additional Fees of the International Searching Authority; PCT/US2016/063292; dated Jan. 31, 2017; 11 Pages; European Patent Office.

Jager et al.; "Transient Recombinant Protein Expression in Mammalian Cells"; Chapter 2; Animal Cell Culture, Cell Engineering 9, pp. 27-64; 2015.

Karlsson et al.; "High-Activity P-Glycoprotein, Multidrug Resistance Protein 2, and Brest Cancer Resistance Protein Membrane Vesicles Prepared From Transiently Transfected Human Embryonic Kidney 293-Epstein-Barr Virus Nuclear Antigen Cells"; Drug Metabolism and Disposition; vol. 38, No. 4; pp. 705-714; 2010.

Keppler et al.; "Transport Function and Substrate Specificity of Multidrug Resistance Protein"; Methods in Enzymology, vol. 292, pp. 607-616; 1998.

Mutsaers et al. (Apr. 2011) PLoS ONE. 6(4):e18439. doi: 10.1372/journal.pone.0018438.

Parham et al.; "Optimization of Transient Gene Expression in Mammalian Cells and Potential for Scale-Up Using Flow Electroporation"; Cytotechnology; 28; pp. 147-155; 1998.

(Continued)

*Primary Examiner* — Robert S Landsman

(74) *Attorney, Agent, or Firm* — Annie J. Morgan

(57) ABSTRACT

The present disclosure relates to method and compositions for generating proteins. In particular, the present disclosure relates to electroporation mediated gene delivery in the generation of recombinant proteins (e.g., drug metabolizing enzyme and transporter vesicles) in mammalian cells.

13 Claims, 10 Drawing Sheets

(56) References Cited

OTHER PUBLICATIONS

Rijpma et al.; "Atovaquone and Quinine Anti-Malarials Inhibit ATP Binding Cassette Transporter Activity"; Malaria Journal, 13, 359; 2014; pp. 1-8.

Schroder et al.; "Overexpression of Recombinant Human Antithrombin III in Chinese Hamster Ovary Cells Results in Malformation and Decreased Secretion of Recombinant Protein"; Biotechnology and Bioengineering, vol. 53, No. 6; 1997, pp. 547-559.

Yang et al. (2018) Journal of Extracellular Vesicles 7(1): pp. 1-15.

Zeng et al.; "Expression of Multidrug Resistance Protein-3 (Multispecific Organic Anion Transporter-D) in Human Embryonic Kidney 293 Cells Confers Resistance to Anticancer Agents"; Cancer Research; 5964-5967; 1999.

Author Unknown (2006). Nature Methods 3(1): pp. 67-68.

Cui Y et al., Drug resistance and ATP-dependent conjugate transport mediated by the apical multidrug resistance protein, MRP2, permanently expressed in human and canine cells, Mol Pharmacol, 1999, 55(5), 929-937.

Hirohashi T et al., Characterization of the Transport Properties of Cloned Rat Multidrug Resistance-associated Protein 3(MRP3), Journal of Biological Chemistry, 1999, 274(21), pp. 15181-15185.

Japanese Patent Application No. 2018-527189, Office Action dated Oct. 19, 2020, 10 pages (5 pages of English Translation and 5 pages of Original Document); Japanese Patent Office.

Kim et al., "Functional Characterization of ABCB4 Mutations Found in Low Phospholipid-Associated Cholelithiasis (LPAC)", Korean J. Physiol Pharmacol., 2013, 17(6), pp. 525-530.

* cited by examiner

CELL FRACTION AND METHOD OF GENERATING A CELL FRACTION CONTAINING A PROTEIN OF INTEREST

This is a divisional application of U.S. patent application Ser. No. 15/778,763 filed on May 24, 2018, now abandoned, which claims the benefit of priority to International Patent Application Serial No. PCT/US16/63292, filed on Nov. 22, 2016, which in turn claims the benefit of priority under 35 U.S.C. § 119 of U.S. Provisional Application Ser. No. 62/259,788 filed on Nov. 25, 2015, the contents of each of which are relied upon and incorporated herein by reference in their entirety.

FIELD OF THE DISCLOSURE

The present disclosure relates to method and compositions for generating proteins. In particular, the present disclosure relates to electroporation mediated gene delivery in the generation of recombinant proteins (e.g., drug metabolizing enzyme and drug transporter vesicles, microsomes or cell fractions) in mammalian cells.

BACKGROUND OF THE DISCLOSURE

Expression of recombinant proteins is important in many aspects of the research, industrial, and pharmaceutical biotechnology industries. For example, the expression of drug metabolizing enzymes and transporter proteins is often critical in drug discovery and development. For many of these proteins, expression in mammalian cells is preferred over expression in prokaryotic cells because of the need for correct post-translational modification (e.g., glycosylation or silation).

Several methods are known for creating host cells that express recombinant proteins. In the most basic methods, a nucleic acid construct containing a gene encoding a heterologous protein and appropriate regulatory regions is introduced into the host cell and allowed to integrate. Methods of introduction include calcium phosphate precipitation, microinjection, and lipofection. In other methods, a selection scheme is used to amplify the introduced nucleic acid construct. In these methods, the cells are co-transfected with a gene encoding an amplifiable selection marker and a gene encoding a heterologous protein (See, e.g., Schroder and Friedl, Biotech. Bioeng. 53(6):547-59 (1997)). After selection of the initial tranformants, the transfected genes are amplified by the stepwise increase of the selective agent (e.g., dihydrofolate reductase) in the culture medium. In some cases, the exogenous gene may be amplified several hundred-fold by these procedures. Other methods of recombinant protein expression in mammalian cells utilize transfection with episomal vectors (e.g., plasmids).

Current methods for creating mammalian cell lines for expression of recombinant proteins suffer from several drawbacks. Such problems include cell toxicity, inability to deliver larger genes or genetic constructs, significant batch-to-batch inconsistency in expression levels, unstable expression, and improper localization, post-translational modification, and/or folding of expressed proteins. Accordingly, what are needed in the art are improved methods for making host cells that express recombinant proteins.

SUMMARY OF THE DISCLOSURE

The present disclosure relates to method and compositions for generating proteins. In particular, the present disclosure relates to electroporation mediated gene delivery in the generation of recombinant proteins (e.g., drug metabolizing enzyme and drug transportervesicles, microsomes or cell fractions) in mammalian cells.

For example, in some embodiments, the present disclosure provides a method of generating membrane-bound proteins, including those in vesicles or microsomes. In some embodiments, the method comprises: a) contacting a mammalian cell (e.g., HEK293, CHO, Hela, S2, MDCK-I, MDCK-II, LLC-PK1, Caco-2, Huh7, and V79 cells) with a nucleic acid encoding a membrane bound protein (e.g., a transporter protein (e.g., ABCB1, ABCB4, ABCB11, ABCC1, ABCC2, ABCC3, ABCC4, ABCC5, ABCC6, ABCG2, or a homolog thereof); b) electroporating the mammalian cell such that the nucleic acid enters said mammalian cell; and c) isolating cell membranes comprising the membrane bound protein of interest.

In some embodiments, the mammalian cell is a human cell. In some embodiments, the cell is a non-human primate cell, a rat cell, a mouse cell, a hamster cell, a dog cell, or a pig cell. In some embodiments, the mammalian cell is a hybridoma.

In some embodiments, the method further comprises the step of culturing the cells after the electroporation step (e.g., in the presence of sodium butyrate). In some embodiments, the isolating step comprises homogenization. In some embodiments, the membrane bound protein of interest comprises post-translational modifications similar to the native membrane bound protein.

In some embodiments, the method further comprises the step of contacting the membrane bound protein with a test compound (e.g., a drug).

Further embodiments provide isolated vesicles or microsomes generated by any of the aforementioned methods.

In some embodiments, the present disclosure provides a method of generating cell fractions (e.g., membrane or cytosolic fractions) comprising proteins of interest. In some embodiments, the protein of interest is a drug metabolizing enzyme (DME). In some embodiments, the DME is a cytochromes P450 (e.g., CYP1A1, CYP1B1, CYP2A6, CYP2B6, CYP1A2, CYP2C8, CYP2C9, CYP2C18, CYP2C19, CYP2D6, CYP2E1, CYP3A5, CYP3A7, CYP3A4, CYP4F2, or CYP2J2), an aldehyde oxidase (AO), a flavin monooxygenase (FMO), a monoamine oxidase A and B (MAO A and B), a N-acetyltransferase (NAT1 and NAT2), a sulfotransferase (SULT1A, SULT1B, SULT1C, SULT1E, SULT2A, SULT2B, SULT4A), an esterase (e.g., carboxylesterase 1 (CES1), carboxylesterase 2 (CES2), paraoxonase 1 (PON1), carboxymethylenebutenolidase (CMBL), butyrylcholinesterase (BChE), arylacetamide deacetylase (AADAC), or alkaline phosphatase (AP)), or a uridine 5'-diphospho-glucuronosyltransferase (UGT) (e.g., UGT1A1, UGT1A3, UGT1A4, UGT1A5, UGT1A6, UGT1A7, UGT1A8, UGT1A9, UGT1A10, UGT2A1, UGT2A2, UGT2A3, UGT2B4, UGT2B7, UGT2B10, UGT2B11, UGT2B15, UGT2B17, or UGT2B28).

Additional embodiments provide a method of screening a test compound, comprising: a) obtaining a protein as described above or herein; and b) contacting the protein with a test compound. In some embodiments, the method further comprises the step of measuring transport of the test compound by a transporter protein. In some embodiments, the measuring comprises measuring kinetics of transport. In some embodiments, the method further comprises the step of assessing modification of a test compound by the protein (e.g., DME).

In some embodiments, the method further comprises the step of contacting the protein with an inhibitor and measuring inhibition of activity, transport, or modification of the substrate by the inhibitor.

Additional embodiments are described herein.

DESCRIPTION OF THE FIGURES

FIG. 8A and FIG. 8B show that recombinant Phase 1 drug metabolizing enzyme Aldehyde Oxidase (AO) prepared with transfected HEK293 cells exhibited standard michaelis-mention kinetics curve when using probe substrate phthalazine.

DEFINITIONS

Figure 1A:
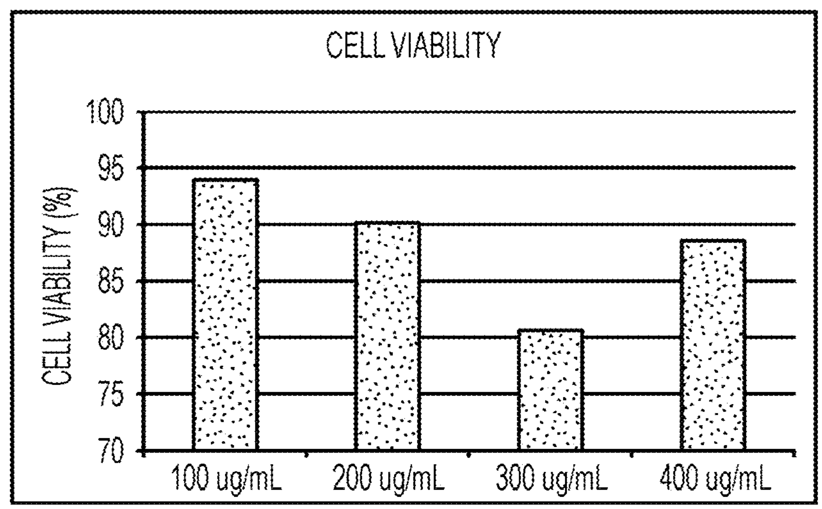
FIG. 1A and FIG. 1B shows the percentage of viable cells following electroporation of adhered HEK293 cells using varying amounts of human MDR1/P-gp DNA (FIG. 1A) and the total amount of viable cells obtained after electroporation and recovery (FIG. 1B).
Figure 1B:
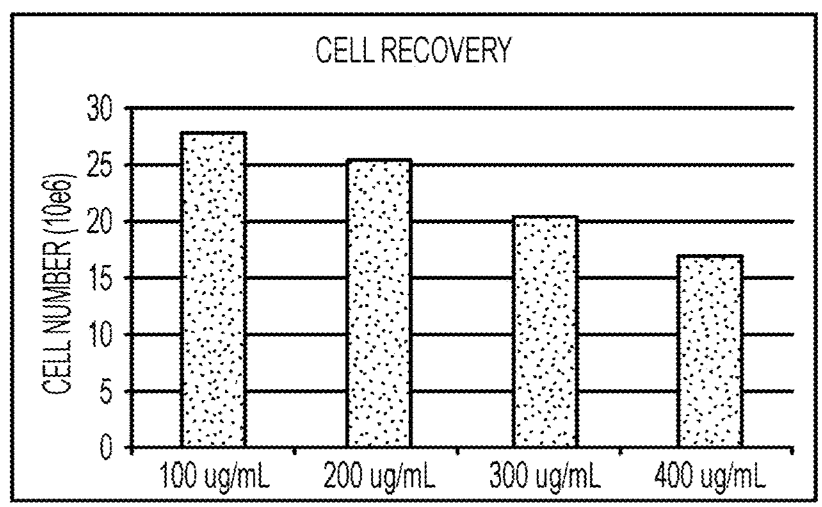
Figure 2A:
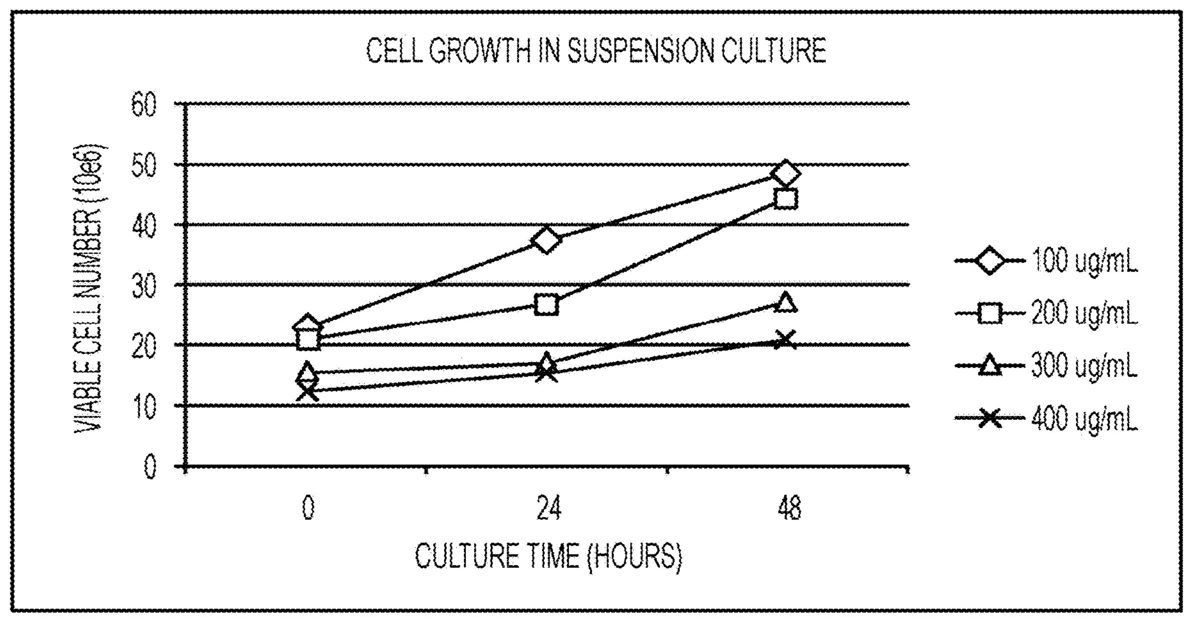
FIG. 2A and FIG. 2B show the total viable cell number at T=0, 24 hr and 48 hrs post EP (FIG. 2A) and the percentage of viable cells (FIG. 2B).
Figure 2B:
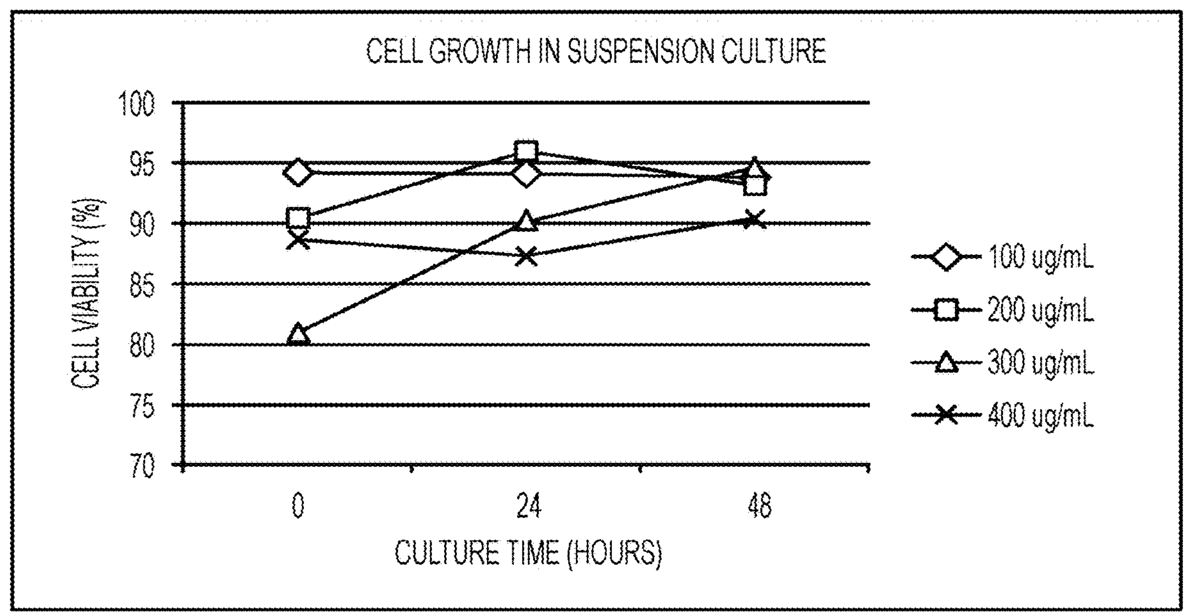

To facilitate understanding of the disclosure, a number of terms are defined below.

As used herein, the term "host cell" refers to any eukaryotic cell (e.g., mammalian cells, avian cells, amphibian cells, plant cells, fish cells, and insect cells), whether located in vitro or in vivo. In some embodiments, the host cell is a mammalian cell (e.g., human cell), including cultured cells, primary cell cultures, and immortalized cell cultures.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "vector" refers to any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

As used herein, the term "genome" refers to the genetic material (e.g., chromosomes) of an organism.

As used herein, the term "protein of interest" or "membrane bound protein of interest" refers to a protein encoded by a nucleic acid of interest.

As used herein, the term "membrane bound protein of interest" refers to a protein that, in its native or non-native state, spans, is bound, or is associated with a cell membrane.

As used herein, the term "exogenous gene" refers to a gene that is not naturally present in a host organism or cell, or is artificially introduced into a host organism or cell.

The term "gene" refers to a nucleic acid (e.g., DNA or RNA) sequence that comprises coding sequences necessary for the production of a polypeptide or precursor (e.g., proinsulin). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and includes sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' untranslated sequences. The sequences that are located 3' or downstream of the coding region and which are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

As used herein, the terms "nucleic acid molecule encoding," "DNA sequence encoding," "DNA encoding," "RNA sequence encoding," and "RNA encoding" refer to the order or sequence of deoxyribonucleotides or ribonucleotides along a strand of deoxyribonucleic acid or ribonucleic acid. The order of these deoxyribonucleotides or ribonucleotides determines the order of amino acids along the polypeptide (protein) chain. The DNA or RNA sequence thus codes for the amino acid sequence.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein the term, the term "in vitro" refers to an artificial environment and to processes or reactions that occur within an artificial environment. In vitro environments can consist of, but are not limited to, test tubes and cell cultures. The term "in vivo" refers to the natural environment (e.g., an animal or a cell) and to processes or reaction that occur within a natural environment.

As used herein, the term "purified" refers to molecules, either nucleic or amino acid sequences, that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated.

The term "test compound" refers to any chemical entity, pharmaceutical, drug, and the like contemplated to be useful in research, diagnostic, or therapeutic applications. Test compounds comprise compounds with both known and unknown properties and activities. A test compound that interacts with the recombinant protein (e.g., transporter protein or drug metabolizing enzyme) can be assessed for any number of properties by screening using the screening methods of the present disclosure.

DETAILED DESCRIPTION OF THE DISCLOSURE

The present disclosure relates to method and compositions for generating proteins. In particular, the present disclosure relates to electroporation mediated gene delivery in the generation of recombinant proteins (e.g., drug metabolizing enzymes and transporters) in mammalian cells.

Several models associated with using recombinant proteins or cells for drug ADME studies are in use. For example, Supersomes™ Drug metabolizing enzyme, ABC (ATP-binding cassette) Transporter vesicles and TransportoCells™ SLC Transporter Cells (Corning, Corning, N.Y.) are insect cell membrane or cytosol fractions containing overexpressed recombinant drug metabolizing enzymes for in vitro assays. ABC transporter vesicles are flipped inside out membrane vesicles (e.g., the functional groups, originally facing to inside of the cells, are flipped to the outside to make it accessible to the drug). ABC vesicles are considered the "gold standard" for studying the involvement of ABC Transporters in drug disposition. Currently, most vesicles are made using insect cell/baculovirus expression system (BEVs) with viral delivery methods. Due to the nature of the BEV expression system, the products can suffer from low activity and inconsistent batch-to-batch performance.

Accordingly, embodiments of the present disclosure provide improved systems and methods for generating recombinant proteins (e.g., drug metabolizing enzyme membrane/cytosolic fraction and ABC transporter vesicles) in mammalian cells (e.g., HEK293 or CHO cells) via electroporation. After being electroporated, the cells are cultured (e.g., for 2-3 days). When the protein of interest is expressed, the expressed protein gets correct post-translational modification, and targeted to the correct location in the cell or cell membrane. After culturing, cells are harvested and cell fractions are prepared (e.g., membrane fractions, cytosolic fractions).

In some embodiments, sodium butyrate is supplemented in the culture post-electroporation to boost the protein expression for higher activity. In some embodiments, sodium butyrate is not employed.

The systems and methods described herein find use in the expression of a variety of drug metabolizing enzymes (DMEs) and drug transportervesicles, microsomes or cell fractions. In some embodiments, the methods described herein find use in expressing "difficult-to-express" complicated membrane proteins that yield low activity in other expression systems (e.g., *E. coli* or insect cells). Vesicles or membrane fractions made by the methods described herein directly addressed the drawbacks of existing vesicle products: the low activity, less "human-like" and large batch-to-batch variation.

The present disclosure is not limited to particular proteins for expression using the systems and methods described herein. Examples include, but are not limited to, DMEs (e.g., in cytosolic or membrane cell fractions) and transporter proteins (e.g., in vesicles).

Examples of DMEs include, but are not limited to, Cytochromes P450 (CYP) (e.g., CYP1A1, CYP1B1, CYP2A6, CYP2B6, CYP1A2, CYP2C8, CYP2C9, CYP2C18, CYP2C19, CYP2D6, CYP2E1, CYP3A5, CYP3A7, CYP3A4, CYP4F2, or CYP2J2), derived from any number of species, aldehyde oxidase (AO), flavin monooxygenase (FMO), monoamine oxidase A and B (MAO A and B), N-acetyltransferase (NAT1 and NAT2), sulfotransferase (SULT1A, SULT1B, SULT1C, SULT1E, SULT2A, SULT2B, SULT4A), esterases (e.g., carboxylesterase 1 (CES1), carboxylesterase 2 (CES2), paraoxonase 1 (PON1), carboxymethylenebutenolidase (CMBL), butyrylcholinesterase (BChE), arylacetamide deacetylase (AADAC), and alkaline phosphatase (AP)) and uridine 5'-diphospho-glucuronosyltransferase (UGT) as shown in Table 1. Exemplary UGT homologs (e.g., rat, mouse, dog and monkey) are shown. The human gene name is listed first. The OMIM accession number for the gene is provided, providing links to nucleic acid and peptide sequences for the wild-type genes and proteins and common allelic variants.

TABLE 1

| Gene name | Full name | OMIM accession number |
|---|---|---|
| UGT1A1 | UDP-GLYCOSYLTRANSFERASE 1 FAMILY, POLYPEPTIDE A1 | 191740 |
| UGT1A3 | UDP-GLYCOSYLTRANSFERASE 1 FAMILY, POLYPEPTIDE A3 | 606428 |
| UGT1A4 | UDP-GLYCOSYLTRANSFERASE 1 FAMILY, POLYPEPTIDE A4 | 606429 |

TABLE 1-continued

| Gene name | Full name | OMIM accession number |
|---|---|---|
| UGT1A5 | UDP-GLYCOSYLTRANSFERASE 1 FAMILY, POLYPEPTIDE A5 | 606430 |
| UGT1A6 | UDP-GLYCOSYLTRANSFERASE 1 FAMILY, POLYPEPTIDE A6 | 606431 |
| UGT1A7 | UDP-GLYCOSYLTRANSFERASE 1 FAMILY, POLYPEPTIDE A7 | 606432 |
| UGT1A8 | UDP-GLYCOSYLTRANSFERASE 1 FAMILY, POLYPEPTIDE A8 | 606433 |
| UGT1A9 | UDP-GLYCOSYLTRANSFERASE 1 FAMILY, POLYPEPTIDE A9 | 606434 |
| UGT1A10 | UDP-GLYCOSYLTRANSFERASE 1 FAMILY, POLYPEPTIDE A10 | 606435 |
| UGT2A1 | URIDINE DIPHOSPHATE GLYCOSYLTRANSFERASE 2 FAMILY, MEMBER A1 | 604716 |
| UGT2A2 | URIDINE DIPHOSPHATE GLYCOSYLTRANSFERASE 2 FAMILY, MEMBER A2 | 604716 |
| UGT2A3 | URIDINE DIPHOSPHATE GLUCURONOSYLTRANSFERASE 2 FAMILY, MEMBER A3 | 616382 |
| UGT2B4 | URIDINE DIPHOSPHATE GLYCOSYLTRANSFERASE 2 FAMILY, MEMBER B4 | 600067 |
| UGT2B7 | URIDINE DIPHOSPHATE GLYCOSYLTRANSFERASE 2 FAMILY, MEMBER B7 | 600068 |
| UGT2B10 | URIDINE DIPHOSPHATE GLYCOSYLTRANSFERASE 2 FAMILY, MEMBER B10 | 600070 |
| UGT2B11 | URIDINE DIPHOSPHATE GLYCOSYLTRANSFERASE 2 FAMILY, MEMBER B11 | 603064 |
| UGT2B15 | URIDINE DIPHOSPHATE GLYCOSYLTRANSFERASE 2 FAMILY, MEMBER B15 | 600069 |
| UGT2B17 | URIDINE DIPHOSPHATE GLYCOSYLTRANSFERASE 2 FAMILY, MEMBER B17 | 601903 |
| UGT2B28 | URIDINE DIPHOSPHATE GLYCOSYLTRANSFERASE 2 FAMILY, MEMBER B28 | 606497 |

Examples of drug transporters include, but are not limited to, those in the Table 2 below. The human gene name is listed first. Exemplary homologs (e.g., rat, mouse, dog and monkey) are shown as lower case with first letter in capital. The OMIM accession number for the gene is provided, providing links to nucleic acid and peptide sequences for the wild-type genes and proteins and common allelic variants.

TABLE 2

| Gene name | Full name | Homologs | OMIM accession number |
|---|---|---|---|
| ABCB1 | ATP-BINDING CASSETTE, SUBFAMILY B, MEMBER 1 | MDR1/Mdr1, P-gp (Rat and Mouse has two isoform: Mdr1a and Mdr1b) | 171050 |
| ABCB4 | ATP-BINDING CASSETTE, SUBFAMILY B, MEMBER 4 | MDR3/Mdr3 | 171060 |
| ABCB11 | ATP-BINDING CASSETTE, SUBFAMILY B, MEMBER 11 | BSEP/Bsep | 603201 |
| ABCC1 | ATP-BINDING CASSETTE, SUBFAMILY C, MEMBER 1 | MRP1/Mrp1 | 158343 |
| ABCC2 | ATP-BINDING CASSETTE, SUBFAMILY C, MEMBER 2 | MRP2/Mrp2, cMOAT | 601107 |
| ABCC3 | ATP-BINDING CASSETTE, SUBFAMILY C, MEMBER 3 | MRP3/Mrp3 | 604323 |
| ABCC4 | ATP-BINDING CASSETTE, SUBFAMILY C, MEMBER 4; ABCC4 | MRP4/Mrp4 | 605250 |
| ABCC5 | ATP-BINDING CASSETTE, SUBFAMILY C, MEMBER 5 | MRP5/Mrp5 | 605251 |
| ABCC6 | ATP-BINDING CASSETTE, SUBFAMILY C, MEMBER 6 | MRP6/Mrp6 | 603234 |
| ABCG2 | ATP-BINDING CASSETTE, SUBFAMILY G, MEMBER 2 | BCRP/Bcrp, MXR | 603756 |

By using electroporation, the gene delivery method is much more controlled (versus the viral delivery method used with the BEVs system), which provides greater batch-to-batch consistency. In addition, using mammalian cells, the recombinant protein is more "human-like" and contemplated to have more activity per mg protein (e.g., versus expression via BEVs or *E. coli*, where a large portion of the expressed protein is non-functional due to improper post-translational modification). For example, experiments conducted during the development of the disclosure showed that UGT1A1 expressed using the electroporation method described herein was 5× more active than UGT1A1 expressed with the BEVs system. In addition, using the existing BEVs method, it takes 6-8 months to develop a new vesicle or a new DME microsome/cytosolic fraction; by using the electroporation methods described herein, the development time can be significantly reduced to 2-3 months.

The host cell cultures of the present disclosure are prepared in a media suitable for the particular cell being cultured. Commercially available media such as Ham's F10 (Sigma, St. Louis, Mo.), Minimal Essential Medium (MEM, Sigma), RPMI-1640 (Sigma), and Dulbecco's Modified Eagle's Medium (DMEM, Sigma) are exemplary nutrient solutions. Suitable media are also described in U.S. Pat. Nos. 4,767,704; 4,657,866; 4,927,762; 5,122,469; 4,560,655; and WO 90/03430 and WO 87/00195; the disclosures of which are herein incorporated by reference. Any of these media may be supplemented as necessary with serum, hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as gentamycin (gentamicin), trace elements (defined as inorganic compounds usually present at final concentrations in the micromolar range) lipids (such as linoleic or other fatty acids) and their suitable carriers, and glucose or an equivalent energy source. Any other necessary supplements may also be included at appropriate concentrations that would be known to those skilled in the art. For mammalian cell culture, the osmolality of the culture medium is generally about 290-330 mOsm.

The present disclosure also contemplates the use of a variety of culture systems (e.g., petri dishes, T-flasks, multi-flasks, multi-well plates, roller bottles, and bioreactors) for the transfected host cells. For example, the transfected host cells can be cultured in a perfusion system. Perfusion culture refers to providing a continuous flow of culture medium through a culture maintained at high cell density. The cells are suspended and do not require a solid support to grow on. Generally, fresh nutrients are supplied continuously with concomitant removal of toxic metabolites and, ideally, selective removal of dead cells. Filtering, entrapment and microcapsulation methods are all suitable for refreshing the culture environment at sufficient rates.

As another example, in some embodiments a fed batch culture procedure can be employed. In the preferred fed batch culture the mammalian host, cells and culture medium are supplied to a culturing vessel initially and additional culture nutrients are fed, continuously or in discrete increments, to the culture during culturing, with or without periodic cell and/or product harvest before termination of culture. The fed batch culture can include, for example, a semi-continuous fed batch culture, wherein periodically whole culture (including cells and medium) is removed and replaced by fresh medium. Fed batch culture is distinguished from simple batch culture in which all components for cell culturing (including the cells and all culture nutrients) are supplied to the culturing vessel at the start of the culturing process. Fed batch culture can be further distinguished from perfusion culturing insofar as the supernatant is not removed from the culturing vessel during the process (in perfusion culturing, the cells are restrained in the culture by, e.g., filtration, encapsulation, anchoring to microcarriers etc. and the culture medium is continuously or intermittently introduced and removed from the culturing vessel).

Further, the cells of the culture may be propagated according to any scheme or routine that may be suitable for the particular host cell and the particular production plan contemplated. Therefore, the present disclosure contemplates a single step or multiple step culture procedure. In a single step culture the host cells are inoculated into a culture environment and the processes of the instant disclosure are employed during a single production phase of the cell culture. Alternatively, a multi-stage culture is envisioned. In the multi-stage culture cells may be cultivated in a number of steps or phases. For instance, cells may be grown in a first step or growth phase culture wherein cells, possibly removed from storage, are inoculated into a medium suitable for promoting growth and high viability. The cells may be maintained in the growth phase for a suitable period of time by the addition of fresh medium to the host cell culture.

Fed batch or continuous cell culture conditions are devised to enhance growth of the mammalian cells in the growth phase of the cell culture. In the growth phase cells are grown under conditions and for a period of time that is maximized for growth. Culture conditions, such as temperature, pH, dissolved oxygen ($dO_2$) and the like, are those used with the particular host and will be apparent to the ordinarily skilled artisan. Generally, the pH is adjusted to a level between about 6.5 and 7.5 using either an acid (e.g., $CO_2$) or a base (e.g., $Na_2CO_3$ or NaOH). A suitable temperature range for culturing mammalian cells such as CHO cells is between about 30° to 38° C. and a suitable $dO_2$ is between 5-90% of air saturation.

Following the polypeptide production phase, the polypeptide or membranes (e.g., vesicles or microsomes) comprising protein of interest is recovered from the culture medium using techniques which are well established in the art.

The present disclosure is not limited to particular methods of isolating lipid vesicles. Exemplary methods are described, for example, in U.S. Pat. No. 8,747,869; U.S. Pat. App. Nos. 20120093885, US20150141634, and US20140080131; each of which is herein incorporated by reference in its entirety.

In some embodiments, proteins expressed using the method described herein and membrane vesicles comprising the proteins find use in drug screening applications (e.g., to screen for toxicity, activity, transport into a cell, kinetic assays, inhibitor assays, or identification of metabolites) of drugs and drug candidates.

In an aspect (1), the disclosure provides a method of generating a vesicle that expresses a membrane bound protein, comprising: a) contacting a mammalian cell with a nucleic acid encoding a membrane bound protein selected from the group consisting of: ABCB1, ABCB4, ABCB11, ABCC1, ABCC2, ABCC3, ABCC4, ABCC5, ABCC6, ABCG2, and a homolog thereof; b) electroporating said mammalian cell such that said nucleic acid enters said mammalian cell; and c) isolating vesicles expressing said membrane bound protein of interest. In an aspect (2), the disclosure provides the method of aspect 1, further comprising the step of culturing said cells after said electroporation step. In an aspect (3), the disclosure provides the method of aspect 2, wherein said culturing comprises addition of sodium butyrate. In an aspect (4), the disclosure provides the method of any one of aspects 1 to 3, wherein said isolating step comprises homogenization of said cells. In an aspect (5), the disclosure provides the method of any one of aspects 1 to 4, wherein said membrane bound protein comprises post-translational modifications similar to the membrane bound protein in native form. In an aspect (6), the disclosure provides the method of any one of aspects 1 to 5, wherein said mammalian cell is a HEK293, CHO, Hela, S2, MDCK-I, MDCK-II, LLC-PK1, Caco-2, Huh7, or V79 cell. In an aspect (7), the disclosure provides the method of any one of aspects 1 to 6, further comprising the step of contacting said vesicle with a test compound. In an aspect (8), the disclosure provides the method of aspect 7, wherein said test compound is a drug.

In a further aspect (9), the disclosure provides a method of screening a test compound, comprising: a) contacting a mammalian cell with a nucleic acid encoding a transporter protein selected from the group consisting of ABCB1, ABCB4, ABCB11, ABCC1, ABCC2, ABCC3, ABCC4, ABCC5, ABCC6, ABCG2, and a homolog thereof; b) electroporating said mammalian cell such that said nucleic acid enters said mammalian cell; c) isolating cell membranes expressing said transporter protein; and d) contacting said cell membranes with said test compound. In an aspect (10), the disclosure provides the method of aspect 9, further comprising the step of measuring transport of said test compound by said transporter protein. In an aspect (11), the disclosure provides t the method of aspect 10, wherein said measuring comprises measuring kinetics of transport. In an aspect (12) the disclosure provides the method of any one of aspects 9 to 11, further comprising the step of contacting said cell membrane with an inhibitor of said drug transporters and measuring inhibition of activity or transport of said drug transporters by said inhibitor. In an aspect (13) the disclosure provides an isolated vesicle produced by the method of any one of aspects 1 to 6. In an aspect (14), the disclosure provides a method of generating a cell fraction containing a protein of interest, comprising: a) contacting a mammalian cell with a nucleic acid encoding a drug metabolizing enzyme selected from the group consisting of a cytochromes P450, an aldehyde oxidase (AO), a flavin monooxygenase (FMO), a monoamine oxidase A and B (MAO A and B), an esterase, a N-acetyltransferase (NAT), a sulfotransferase (SULT), a uridine 5'-diphospho-glucuronosyltransferase (UGT), and a homolog thereof; b) electroporating said mammalian cell such that said nucleic acid enters said mammalian cell; and c) isolating a cell fraction containing said drug metabolizing enzyme. In an aspect (15) the disclosure provides the method of aspect 14, wherein said cytochrome P450 is selected from the group consisting of CYP1A1, CYP1B1, CYP2A6, CYP2B6, CYP1A2, CYP2C8, CYP2C9, CYP2C18, CYP2C19, CYP2D6, CYP2E1, CYP3A5, CYP3A7, CYP3A4, CYP4F2, and CYP2J2. In an aspect (16) the disclosure provides the method of aspect 14, wherein said esterase is selected from the group consisting of carboxylesterase 1 (CES1), carboxylesterase 2 (CES2), paraoxonase 1 (PON1), carboxymethylenebutenolidase (CMBL), butyrylcholinesterase (BChE), arylacetamide deacetylase (AADAC), and alkaline phosphatase (AP). In an aspect (17), the disclosure provides the method of aspect 14, wherein said UGT is selected from the group consisting of UGT1A1, UGT1A3, UGT1A4, UGT1A5, UGT1A6, UGT1A7, UGT1A8, UGT1A9, UGT1A10, UGT2A1, UGT2A2, UGT2A3, UGT2B4, UGT2B7, UGT2B10, UGT2B11, UGT2B15, UGT2B17, and UGT2B28. In an aspect (18), the disclosure provides the method of any one of aspects 14 to 17, further comprising the step of culturing said cells after said electroporation step. In an aspect (19), the disclosure provides the method of aspect 18, where said culturing comprises addition of sodium butyrate. In an aspect (20) the disclosure provides the method of any one of aspects 14 to 19, wherein said isolating step comprises homogenization of said cells. In an aspect (21) the disclosure provides the method of any one of aspects 14 to 20, wherein drug metabolizing enzyme comprises post-translational modifications similar to the drug metabolizing enzyme in native form. In an aspect (22) the disclosure provides the method of any one of aspects 14 to 21, wherein said mammalian cell is a HEK293, CHO, Hela, S2, MDCK-I, MDCK-II, LLC-PK1, Caco-2, Huh7, or V79 cell. In an aspect (23) the disclosure provides the method of any one of aspects 14 to 22, wherein said cell fraction is a cytosolic fraction. In an aspect (24) the disclosure provides the method of any one of aspects 14 to 22, wherein said cell fraction is a membrane fraction. In an aspect (25) the disclosure provides the method of any one of aspects 14 to 24, further comprising the step of contacting said cell fraction with a test compound. In an aspect (25) the disclosure provides the method of aspect 25, wherein said test compound is a drug. In an aspect (26) the disclosure provides the method of aspect 26, further comprising the step of assessing modification of said drug. In an aspect (28) the disclosure provides a cell fraction produced by the method of any one of aspects 14 to 24.

EXPERIMENTAL

The following examples serve to illustrate certain preferred embodiments and aspects of the present disclosure and are not to be construed as limiting the scope thereof.

Example 1

Cell Culture—Cell Preparation for Electropration

In brief, on Day 1, 293-F cells were passaged into appropriate sized shaker flasks at a density of 0.7-1.0×$10^6$ cell/ml using supplemented CD293 medium (available from Gibco, Cat. No. 11913-019, Life Technologies Corp., Carlsbad, Calif.) supplemented with 4 mM L-glutamine (available from Gibco, Cat. No. 25030-081, Thermo Fisher Scientific, Inc., Carlsbad, Calif.). Cell viability and cell number were determined using a Cellometer (available from Nexcelom Bioscience, Lawrence, Mass.).

Electroporation (EP)

On Day 2, cells were subjected to EP. In short, following a determination of cell viability and cell density, cells were pelleted down by spinning at 100 g for 10 min, after which the media was aspirated and cells resuspended in EP Buffer (available from MaxCyte, Cat. No. B201, MaxCyte Inc., Gaithersburg, Md.). The cell suspension was pelleted down again by spinning at 100 g for 10 min, then resuspended in an appropriate amount of EP Buffer to reach 100×$10^6$ cells/ml which was used as the cell stock. cDNA's to be used for EP were prepared in sterile water at a final concentration of 5 mg/ml. For each sample used for OC-400 processing assembly, 0.4 ml of cell stock and DNA was placed in a sterile 1.5 ml eppendorf tube resulting in a final concentration of 100 μg/ml, 200 μg/ml, 300 μg/ml or 400 μg/ml DNA as indicated in the tables and cell density of 40×106 cells per sample. For each sample used for CL-2 processing assembly, 40 ml of cell stock and DNA was placed in 50 ml sterile conical tube resulting in a final concentration of 300 μg/ml DNA.

All Samples were transferred into an OC-400 processing assembly or CL-2 processing assembly (available from MaxCyte Inc., Gaithersburg, Md.) following the manufacture instructions for EP of HEK cells. Following EP, the cells were carefully pipetted out and transferred into the bottom of appropriate size of shaker flasks and incubated for 20 min at 37° C. with 8% $CO_2$, after which appropriate amount of pre-warmed culture media was added into the shaker flasks to reach cell density at 1×$10^6$ cells/ml. The cells were incubated for 0.5 to 1 hr at 37° C. with 8% $CO_2$. Cell viability and cell density were determined after the incubation.

Cell Recovery

For small scale experiment, a portion of cells (e.g., 5×$10^6$ cells) was taken out from the culture and spun down at 100 g for 10 min and plated onto Corning Biocoat™poly-D-lysine coated T-flask or TC treated T-flask (available from Corning, Corning, N.Y.) in plating media (DMEM, high glucose supplemented with 1×MEM non-essential amino acid and 10% Fetal Bovine Serum, available from Mediatech, Inc., Manassas, Va.) and cultured at 37° C. with 8% $CO_2$; the rest of cells were spun down at 100 g for 10 min and then resuspended in 25 mL pre-warmed supplemented CD293 media and cultured at 37° C. with 8% $CO_2$. Cell viability and density were determined for suspension cultured cells every 24 hrs. After 48 hours or appropriate incubation time, the cells cultured in suspension was spun down at 100 g for 10 min; the cells cultured in adhesion format were harvested either by PBS (for TC-treated T-flasks) or by incubating with 2 ml of 0.25% trypsin with EDTA for 2-3 min, then neutralized with plating media (PDL-treated T-flasks). Cell suspension was spun down at 100 g for 10 min. For large scale experiment, after EP and recovery, the cells were cultured in 2 L shaker flask. After 24 hrs, 100 mL of fresh CD293 media supplemented with or without 2 mM sodium butyrate was added into each flask. The cells were harvested at 48 hrs by spinning down at 100 g for 10 min.

Vesicle Preparation

Crude plasma membrane vesicles were prepared as following. Briefly, the cells pellets obtained from the cell recovery step were washed once with phosphate buffered saline (PBS) and centrifuged at 1500 rpm for 10 min at 4° C. The resulting pellet was diluted with appropriate amount (4×pellet weight) of TMEP buffer (50 mM Tris-Base, 50 mM Mannitol, 2 mM EGTA, 2 mM 2-Mercaptoethanol, pH 7.0) supplemented with a 1:500 dilution of Protease Inhibitor Cocktail (available from Sigma, Cat. No. P8340, St. Louis, Mo.) and transferred into Dounce Homogenizer, and manually homogenized with 10 stokes. The cell lysate was centrifuged at 2600 rpm for 10 minutes at 4° C. The supernatant was transferred to a new set of centrifuge tube and spun at 37,000 rpm for 15 minutes at 4° C. The resulting pellet was resuspended in an appropriate amount of TMEP buffer and homogenized with a Dounce B homogenizer with 10 strokes. The membrane vesicles were aliquoted and stored at −80° C. until use.

Human Recombinant AO and UGT1A1 Enzyme Preparation

The recombinant AO and UGT1A1 enzymes were prepared as following. Briefly, the cells pellets obtained from the cell recovery step were washed once with phosphate buffered saline (PBS) and centrifuged at 1500 rpm for 10 min at 4° C. The resulting pellet was diluted with appropriate amount of 0.1 M potassium phosphate buffer, and transferred into Dounce Homogenizer followed with 10 stokes. The cell lysate was centrifuged at 2600 rpm for 10 minutes at 4° C. The supernatant was transferred to a new set of centrifuge tube and spun at 37,000 rpm for 15 minutes at 4° C. For recombinant AO, the supernatant (soluble fraction) was aliquoted and stored at −80° C. until use. For UGT1A1 microsomes, the pellet was resuspended in an appropriate amount of 0.1M Tris buffer and homogenized with a Dounce homogenizer with 10 strokes. The UGT1A1 microsomes were aliquoted and stored at −80° C. until use.

Transporter Uptake Assay

N-methyl-quinidine (NMQ) (available from Sigma, St. Louis, Mass.) was used as the probe substrate for MDR1/P-gp vesicles uptake assay at final concentration of 5 μM; estrone-3-sulfate (E3S) was used as probe substrate for BCRP vesicles uptake assay at final concentration of 1 μM consisting of 1% of [$^3$H] estrone-3-sulfate (available from Perkin Elmer, Waltham, Mass.) and 99% of cold estrone-3-sulfate (available from Sigma, St. Louis, Mass.); 5(6)-carboxy-2,'7'-dichlorofluorescein (CDCF) (available from Thermo Fisher Scientific, Inc., Carlsbad, Calif.) was used as probe substrate for MRP2 vesicles at final concentration of 5 μM. A 60 μl reaction mixture containing 50 μg vesicles and probe substrate at 1.25× of the final concentration and 2.5 mM GSH (only for MRP2) in uptake buffer (47 mM MOPs, 65 mM KCl and 7 mM MgCl2, pH 7.4) was pre-incubated at 37° C. for 5 minutes. The uptake was initiated by addition of 5 mM ATP or AMP, followed by 5 minutes incubation for MDR1 vesicles, 3 minutes for BCRP vesicles and 15 minutes for MRP2 vesicles at 37° C. The assay was terminated by transferring the reaction solution onto glass fiber (G/F) filter plate (available from EMD-Millipore, Cat. No. MSFBN6B10, Billerica, Mass.) through vacuum manifold (Available from EMD-Millipore, Billerica, Mass.), then the filter plate was washed five times with cold washing buffer (40 mM MOPs and 70 mM KCl, pH 7.4). After drying the filter plate for 1-2 hr at room temperature in the dark, for BCRP vesicle, 50 μL of scintillation fluid (Available from Perkin Elmer, Optiphase Supermix, Waltham, Mass.) was added into the sample wells. The plate was directly read on Microbeta scintillation counter (available from Perkin Elmer, Waltham, Mass.). For MDR1/P-gp vesicles, 100 μL of 10% SDS was added into the sample wells; for MRP2 vesicles, 100 μL of 0.1N NaOH was added into the sample wells. After 10 min incubation at room temperature, the filter plate was put onto a 96-well plate (available from Corning Life Sciences, Tewksbury, Mass.) and spun at 2000 rpm for 5 min, the released compound was eluted into the 96-well receiver plate. For CDCF uptake in MRP2 vesicles, the fluorescence was measured directly on a fluorescence reader Safire$^2$ (available from Tecan) at Ex 485 nm, Em 538 nm. For NMQ uptake in MDR1/P-gp vesicles, 100 ul of 0.1N $H_2SO_4$ was added into each well, then fluorescence was measured using a fluorescence plate reader Safire$^2$ at Ex 355 nm, Em 448 nm.

AO Assay

AO assays are carried out at 37° C. in 25 mM potassium phosphate buffer (pH7.4) containing 0.1 mM EDTA. 170 μL assay buffer was mixed with 20 μL 1 mM phthalazine and prewarmed to 37° C. in heat block. The reaction is initiated with 10 μL 5 mg/mL AO sample. The cap needs to be opened for oxygen circulation. After incubation, the reaction was stopped by the addition of 100 ul 94% acetonitrile/6% glacial acetic acid. The reaction mix was centrifuged (10,000×g) for 3 minutes and supernatant was analyzed on HPLC.

UGT1A1 Assay

A 0.2 ml reaction mixture containing 1.0 mg/ml protein, 2 mM uridine diphosphoglucuronic acid (UDPGA), 10 mM magnesium chloride, 0.025 mg/ml alamethicin and 150 uM beta-estradiol in 50 mM Tris (pH 7.5) was incubated at 37° C. for 30 minutes. After incubation, the reaction was stopped by the addition of 50 ul 94% acetonitrile/6% glacial acetic acid. The reaction mix was centrifuged (10,000×g) for 3 minutes and supernatant was analyzed on HPLC.

Results

Results are shown in FIGS. 1A-10.

Figure 3A:
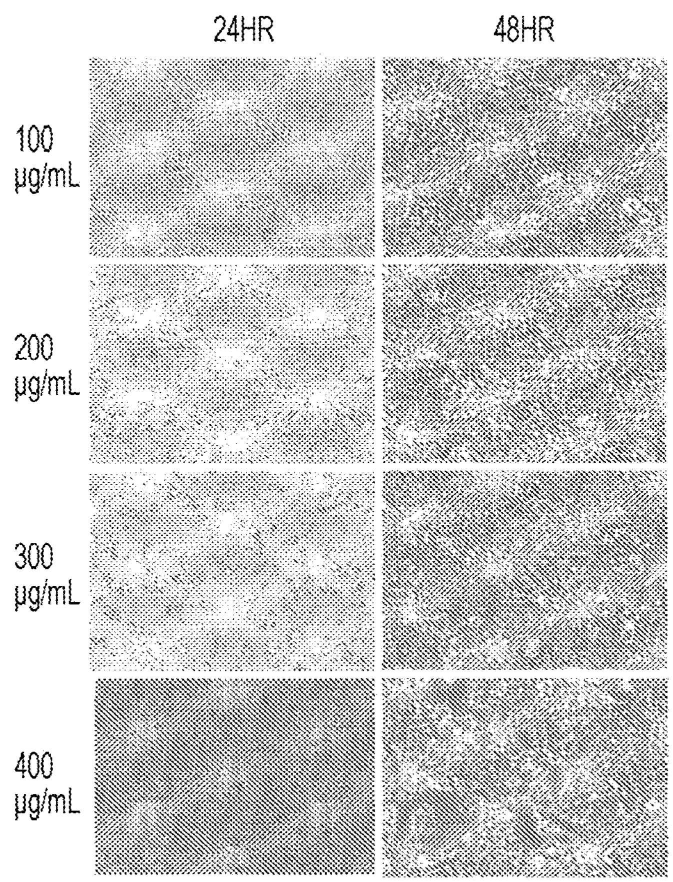
FIG. 3A and FIG. 3B shows photomicrographs of monolayers of cells transfected with increasing amounts of DNA at T=24 hrs and T=48 hrs (FIG. 3A) and a graph recording the percentage of viable cells (FIG. 3B).
Figure 3B:
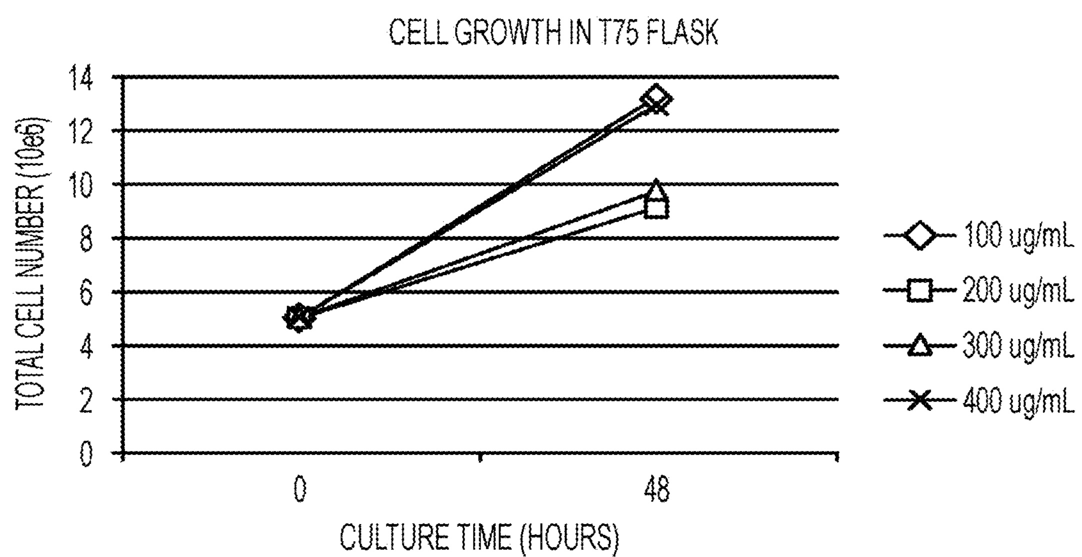

FIGS. 1A-3B show that cells exhibit viability and growth following electroporation. FIG. 1A shows the percentage of viable cells following electroporation of adhered HEK293 cells using varying amounts of human MDR1/P-gp DNA. FIG. 1B shows total amount of viable cells obtained after electroporation and recovery. Viability and recovery were strong across all tested concentrations. FIG. 2A and FIG. 2B shows the total viable cell number at T=0, 24 hr and 48 hrs post electroporation (FIG. 2A) and the percentage of viable cells (FIG. 2B). Cell counts increased over time following electroporation for all four dosages. The percent of viable cells remained high over time. FIG. 3A shows monolayers of cells transfected with increasing amounts of DNA at T=24 hrs and T=48 hrs. The percentage of viable cells were recorded in graph (FIG. 3B). Viable cells increased over time for all for test samples.

Figure 4:
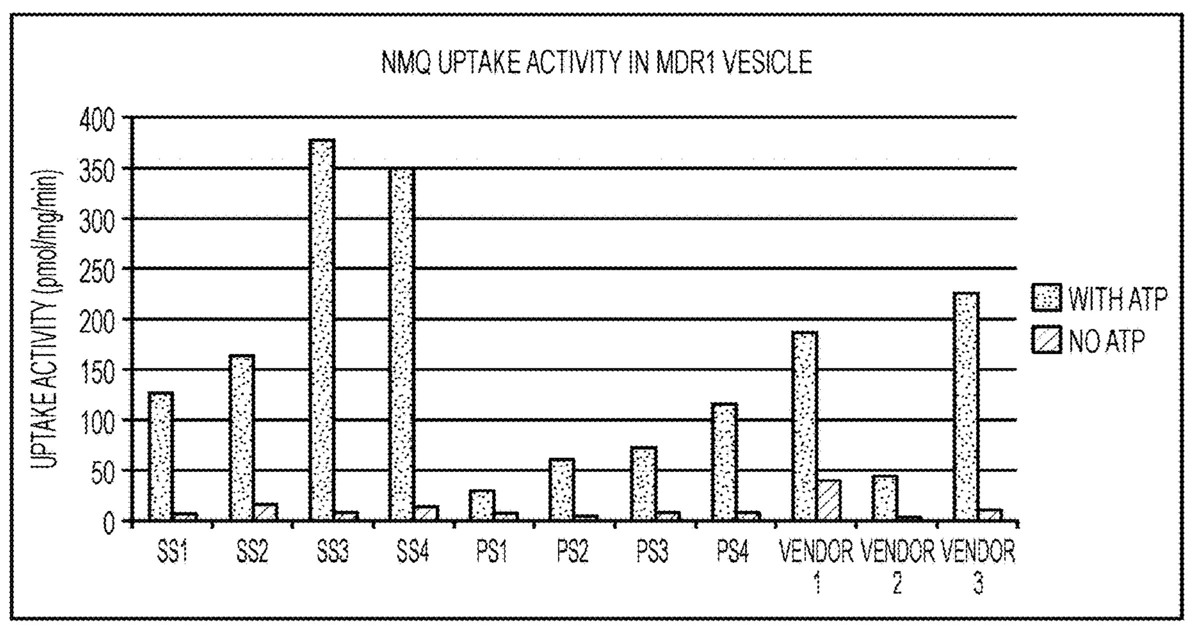
FIG. 4 shows N-methylquinidine (NMQ) uptake activity after 5 minutes incubation with MDR1/P-gp vesicles prepared from HEK293 cells transfected with varying amounts of DNA (100 μg/ml, 200 μg/ml, 300 ug/mL and 400 μg/ml MDR1), cultured in either suspension or adhesion format post electroporation.
Figure 7:
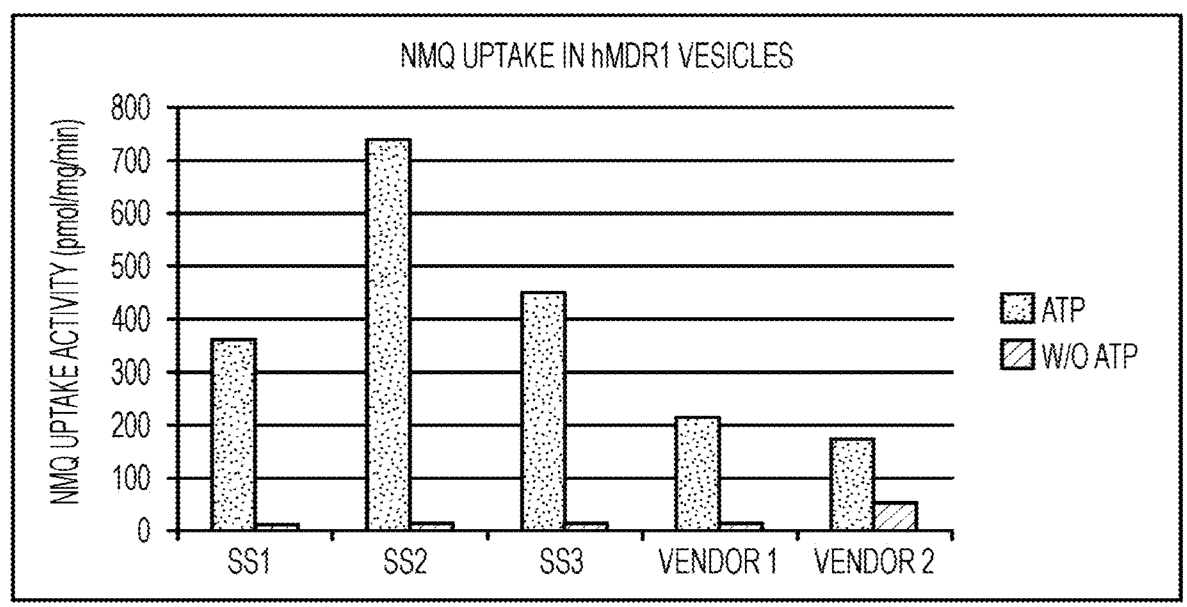
FIG. 7 shows NMQ uptake activity after 5 minutes incubation with MDR1/P-gp vesicles prepared from HEK293 cells transfected with 300 ug/mL MDR1 cDNA using small scale EP device (OC-400) or a large scale EP device (CL-2 bag), and cultured in suspension format post electroporation.

FIGS. 4 and 7 show uptake of N-methylquinidine (NMQ) by vesicles prepared as described above. FIG. 4 shows NMQ uptake activity after 5 minutes incubation with MDR1/P-gp vesicles prepared from HEK293 cells transfected with varying amounts of DNA (100 μg/ml, 200 μg/ml, 300 ug/mL and 400 μg/ml MDR1), cultured in either suspension or adhesion format post electroporation. Quantative results are shown in Table 3, below.

TABLE 3

| Sample # | Culture format | DNA Concentration (ug/mL) | Amount Uptake with ATP (pmol/mg/min) | Amount Uptake without ATP (pmol/mg/min) | S/N |
|---|---|---|---|---|---|
| SS1 | Suspension | 100 | 126.4 | 7.0 | 17.9 |
| SS2 | | 200 | 163.4 | 15.3 | 10.6 |
| SS3 | | 300 | 378.8 | 9.6 | 39.5 |
| SS4 | | 400 | 350.3 | 13.1 | 26.7 |
| PS1 | Adhesion | 100 | 29.1 | 6.9 | 4.2 |
| PS2 | | 200 | 60.3 | 3.9 | 15.4 |
| PS3 | | 300 | 71.2 | 7.6 | 9.4 |
| PS4 | | 400 | 115.3 | 8.2 | 14.1 |
| Vendor 1 | n.a. | n.a. | 187.3 | 39.9 | 4.7 |
| Vendor 2 | n.a. | n.a. | 43.3 | 1.9 | 22.9 |
| Vendor 3 | n.a. | n.a. | 226.5 | 11.8 | 19.2 |

FIG. 7 shows NMQ uptake activity after 5 minutes incubation with MDR1/P-gp vesicles prepared from HEK293 cells transfected with 300 ug/mL MDR1 cDNA using small scale EP device (OC-400) or a large scale EP device (CL-2 bag), and cultured in suspension format post electroporation.

Figure 5:
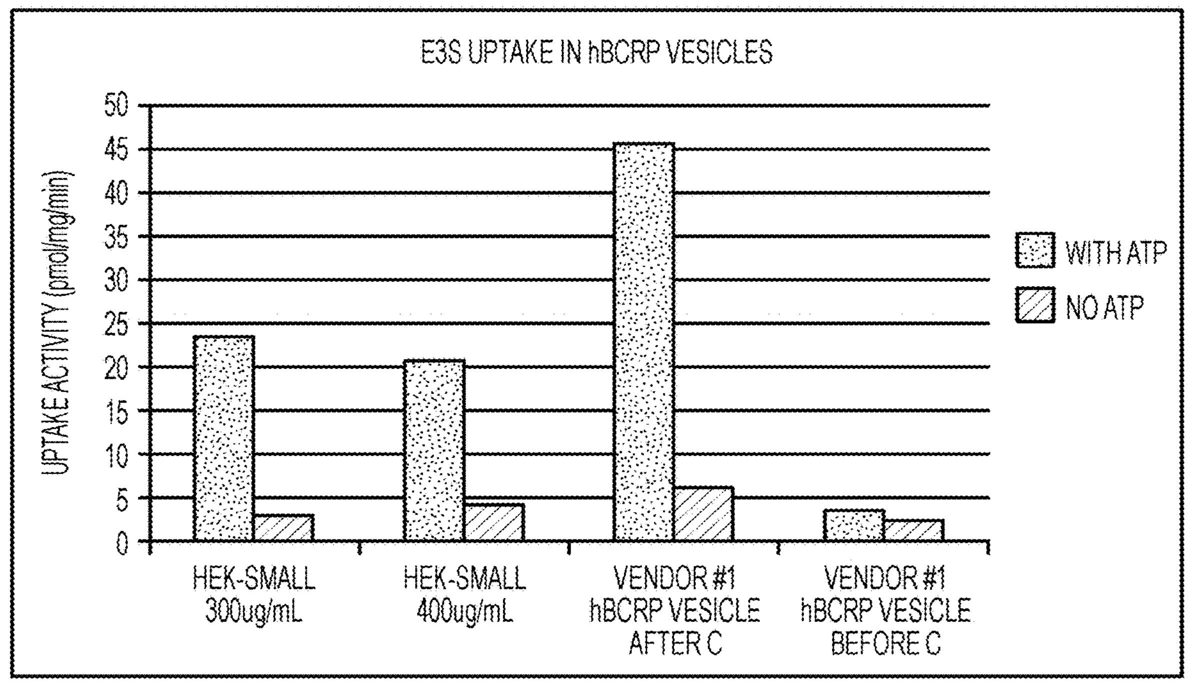
FIG. 5 shows estrone-3-sulfate (E3S) uptake activity in hBCRP vesicles.

FIG. 5 shows uptake of estrone-3-sulfate (E3S) by vesicles prepared as described above. As seen with the vendor samples, uptake activity was only observed after treatment with cholesterol (C) (compare "before C" sample with "after C" sample). In contrast, cholesterol was not needed with the electroporated HEK cells employing methods described herein.

Figure 6:
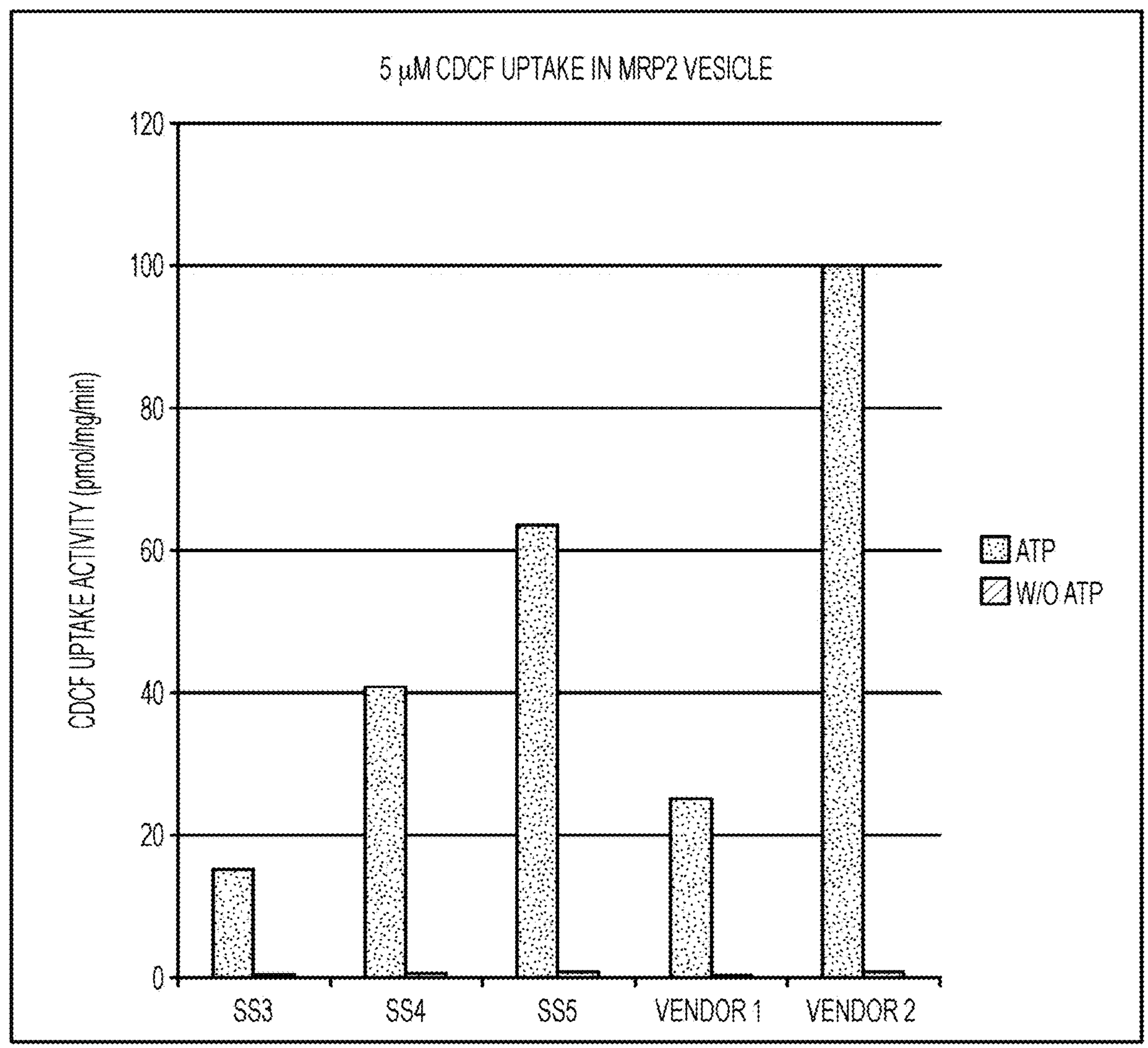
FIG. 6 shows CDCF uptake activity in hMRP2 vesicles.

FIG. 6 shows CDCF uptake in hMRP2 vesicles. Quantitative data are shown in Table 4, below.

TABLE 4

| Sample # | DNA Concentration (ug/mL) | Amount Uptake with ATP (pmol/mg/min) | Amount Uptake without ATP (pmol/mg/min) | S/N |
|---|---|---|---|---|
| SS3 | 200 | 15.4 | 0.6 | 25.7 |
| SS4 | 300 | 41 | 0.8 | 51.3 |
| SS5 | 400 | 63.6 | 0.9 | 70.7 |
| Vendor 1 | n.a. | 24.9 | 0.2 | 124.5 |
| Vendor 2 | n.a. | 100.5 | 0.9 | 111.7 |

Figure 8A:
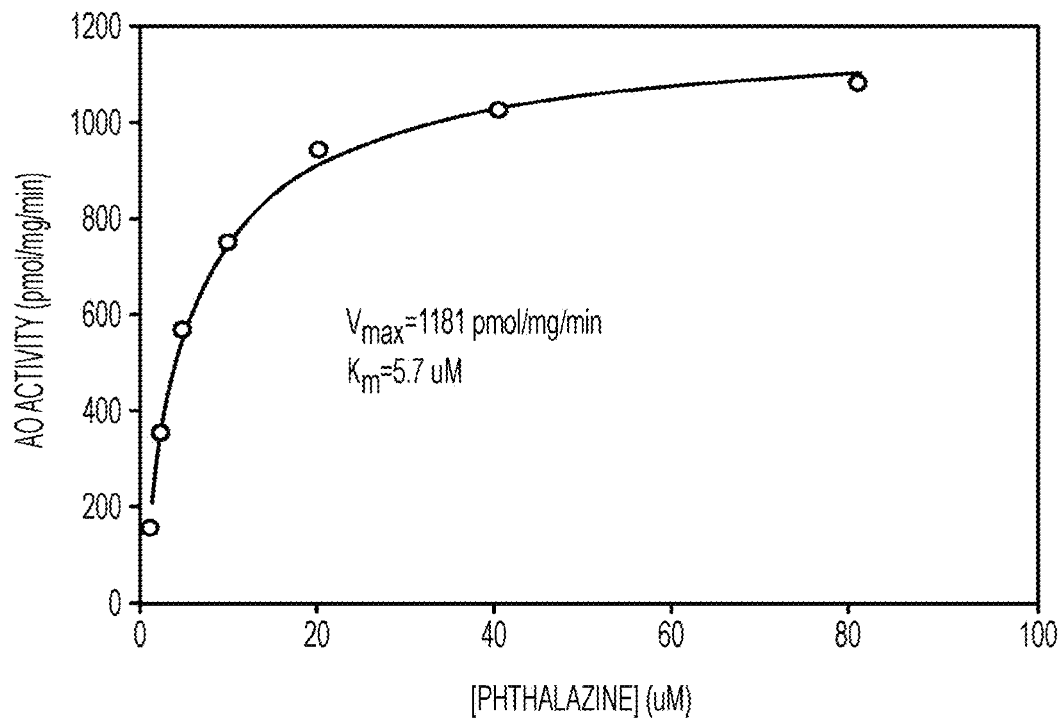
FIG. 8A and FIG. 8B show a graph showing AO activity vs concentration (FIG. 8A) and a graph showing a comparison of Vmax for rAO in HEK293 cells versus a commercially available system (FIG. 8B).
Figure 8B:
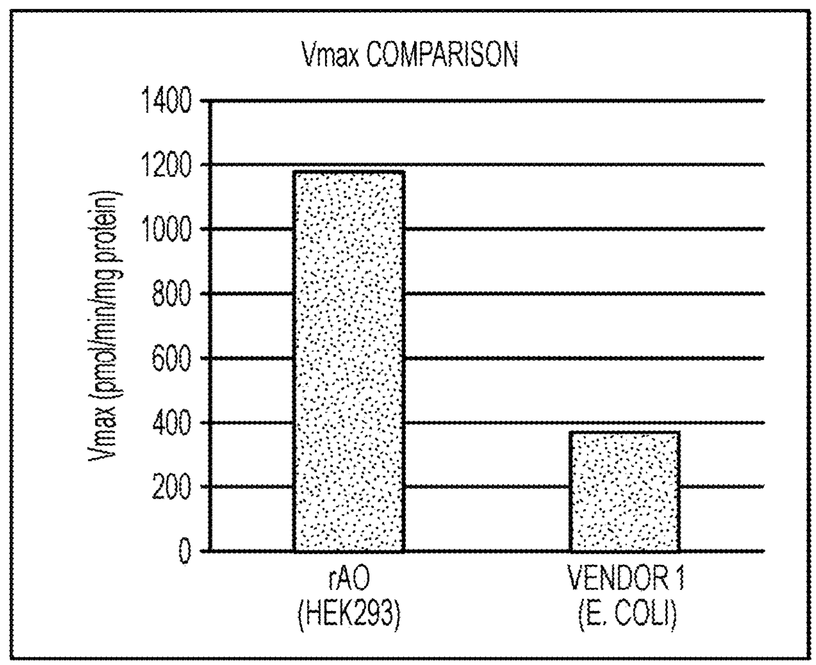

FIG. 8A and FIG. 8B shows activity of AO in cell fractions/cytosol prepared as described above. FIG. 8-A is a graph showing AO activity vs concentration and FIG. 8B is a graph showing a comparison of Vmax for rAO in HEK293 cells versus a commercially available system. FIG. 8A and FIG. 8B show that recombinant Phase 1 drug metabolizing enzyme Aldehyde Oxidase (AO) prepared with transfected HEK293 cells exhibited standard michaelis-mention kinetics curve when using probe substrate phthalazine.

Figure 9A:
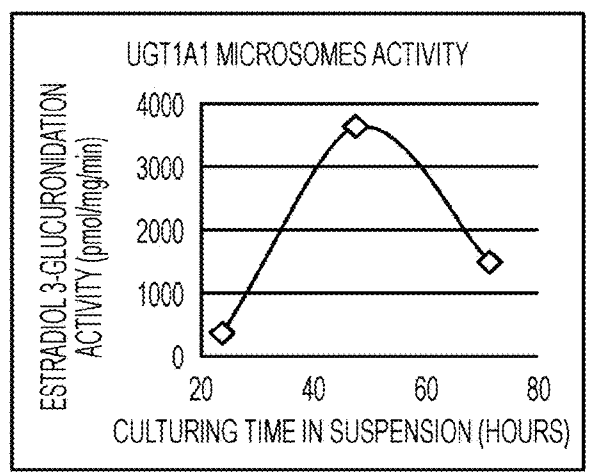
FIG. 9A and FIG. 9B show microsome activity (FIG. 9A) and microsome yield (FIG. 9B) of phase 2 drug metabolizing enzyme UDP-glucuronosyl transferase 1A1 (UGT1A1) cDNA delivered into HEK293 cells with electroporation, followed by culturing for 24 to 72 hours in suspension before harvest.
Figure 9B:
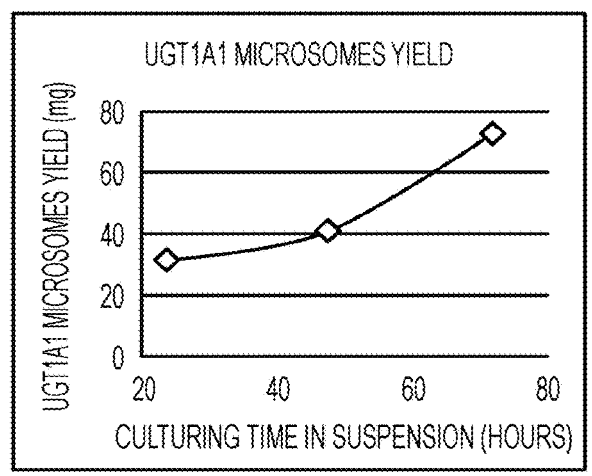
Figure 10:
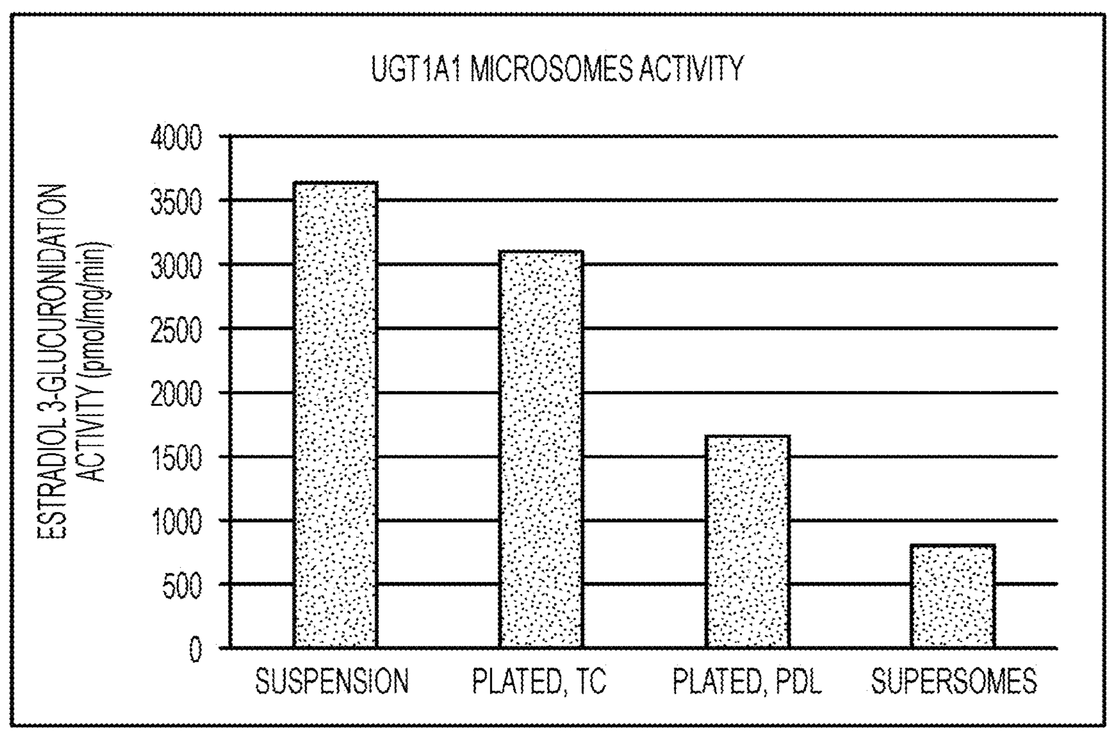
FIG. 10 shows activity of UGT1A1 in HEK293 microsomes.

FIG. 9A, FIG. 9B, and FIG. 10 show UGT1A1 activity in cell fraction/membrane fraction (microsomes) prepared as described above. FIG. 9A and FIG. 9B show microsome activity (FIG. 9A) and microsome yield (FIG. 9B) of phase 2 drug metabolizing enzyme UDP-glucuronosyl transferase 1A1 (UGT1A1) cDNA delivered into HEK293 cells with electroporation, followed by culturing for 24 to 72 hours in suspension before harvest. FIG. 10 shows activity of UGT1A1 in HEK293 microsomes, showing surprising activity as comparted to prior gold standard methods (Supersomes™).

All publications and patents mentioned in the above specification are herein incorporated by reference. Various modifications and variations of the described method and system of the disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure which are obvious to those skilled in the relevant fields are intended to be within the scope of the following claims.

What is claimed is:

1. A method of generating a cell fraction containing a protein of interest, comprising:

a) contacting a mammalian cell with a nucleic acid encoding a drug metabolizing enzyme selected from the group consisting of a cytochromes P450, an aldehyde oxidase (AO), a flavin monooxygenase (FMO), a monoamine oxidase A and B (MAO A and B), an esterase, a N-acetyltransferase (NAT), a sulfotransferase (SULT), a uridine 5'-diphospho-glucuronosyltransferase (UGT), and a homolog thereof;

b) electroporating said mammalian cell such that said nucleic acid enters said mammalian cell;

c) culturing said cell, where said culturing comprises addition of sodium butyrate; and d) isolating a cell fraction containing said drug metabolizing enzyme, thereby generating the cell fraction containing the protein of interest, wherein the generated cell fraction expressing the said metabolizing enzyme has more activity per mg protein than a baculovirus expression system cell fraction.

2. The method of claim 1, wherein said cytochrome P450 is selected from the group consisting of CYP1A1, CYP1B1, CYP2A6, CYP2B6, CYP1A2, CYP2C8, CYP2C9, CYP2C18, CYP2C19, CYP2D6, CYP2E1, CYP3A5, CYP3A7, CYP3A4, CYP4F2, and CYP2J2.

3. The method of claim 1, wherein said esterase is selected from the group consisting of carboxylesterase 1 (CES1), carboxylesterase 2 (CES2), paraoxonase 1 (PON1), carboxymethylenebutenolidase (CMBL), butyrylcholinesterase (BChE), arylacetamide deacetylase (AADAC), and alkaline phosphatase (AP).

4. The method of claim 1, wherein said UGT is selected from the group consisting of UGT1A1, UGT1A3, UGT1A4, UGT1A5, UGT1A6, UGT1A7, UGT1A8, UGT1A9, UGT1A10, UGT2A1, UGT2A2, UGT2A3, UGT2B4, UGT2B7, UGT2B10, UGT2B11, UGT2B15, UGT2B17, and UGT2B28.

5. The method of claim 1, wherein said isolating step comprises homogenization of said cells.

6. The method of claim 1, wherein the drug metabolizing enzyme comprises post-translational modifications similar to the drug metabolizing enzyme in native form.

7. The method of claim 1, wherein said mammalian cell is HEK293, CHO, Hela, S2, MDCK-I, MDCK-II, LLC-PK1, Caco-2, Huh7, or V79 cell.

8. The method of claim 1, wherein said cell fraction is a cytosolic fraction.

9. The method of claim 1, wherein said cell fraction is a membrane fraction.

10. The method of claim 1, further comprising the step of contacting said cell fraction with a test compound.

11. The method of claim 10, wherein said test compound is a drug.

12. The method of claim 11, further comprising the step of assessing modification of said drug.

13. A cell fraction produced by the method of claim 1.

* * * * *